United States Patent [19]

Bleile et al.

[11] 4,448,888
[45] May 15, 1984

[54] COMPOSITIONS AND METHOD FOR CORRECTING TEMPERATURE DEPENDENCE OF HEMOGLOBIN ASSAYS

[75] Inventors: Dennis M. Bleile, Emeryville; Diane M. Allen, Richmond; Steve K. Tanaka, Vallejo; Francis J. Matarrese, Jr., Oakland, all of Calif.

[73] Assignee: Bio-Rad Laboratories, Inc., Richmond, Calif.

[21] Appl. No.: 411,112

[22] Filed: Aug. 24, 1982

[51] Int. Cl.³ .................. G01N 33/72; G01N 33/66
[52] U.S. Cl. .................................. 436/67; 436/14; 436/15; 436/16; 436/66; 436/87; 436/161; 436/176
[58] Field of Search .................. 436/14, 15, 16, 66, 436/67, 87, 161, 176

[56] References Cited

U.S. PATENT DOCUMENTS

| | | | |
|---|---|---|---|
| 3,519,572 | 7/1970 | Kita | 436/15 |
| 3,629,142 | 12/1971 | Marbach | 436/14 X |
| 3,964,865 | 6/1975 | Das | 23/230 B |
| 4,142,855 | 3/1979 | Acuff | 23/230 B |
| 4,142,856 | 3/1979 | Acuff | 23/230 B |
| 4,142,857 | 3/1979 | Acuff | 23/230 B |
| 4,142,858 | 3/1979 | Acuff | 23/230 B |
| 4,168,147 | 9/1979 | Acuff | 23/230 B |
| 4,189,401 | 2/1980 | Louderbach | 436/14 X |
| 4,230,601 | 10/1980 | Hill | 436/14 |
| 4,238,196 | 12/1980 | Acuff | 23/230 B |
| 4,250,051 | 2/1981 | Armstrong | 436/15 |
| 4,260,516 | 4/1981 | Moore | 436/15 |

OTHER PUBLICATIONS

M. W. Johnson et al., Clinica Chimica Acta, 104, 319-328, (1980).
"Simple Method for Estimating Glycosylated Hemoglobins, and Its Application to Evaluation of Diabetic Patients," Clin. Chem. 24/10, 1708-1710, (1978).
"The Glycosylation of Hemoglobin: Relevance to Diabetes Mellitus," Science, vol. 200, Apr. 7, 1978.
"Preparation of Lyophilized Abnormal Hemoglobin Controls for Cellulose Acetate Electrophoresis," Amer. J. Clin. Pathologists, vol. 74; pp. 64-67, (1980).
"Lyophilization of Hemoglobin and the Stability of the Lyophilysates," Clin. Chemistry, vol. 26, pp. 1926-1927, (1980).
4 unnumbered pp. Biomedix literature, Jan. 1979.
Pp. 1-6, Leeco Diagnostics, Inc. literature, "Glyco-Hemoglobin," Jul. 1980.

*Primary Examiner*—Sidney Marantz
*Attorney, Agent, or Firm*—Townsend and Townsend

[57] ABSTRACT

Artificially constituted storage-stable hemoglobin compositions for use in the temperature correction of a cation exchange column chromatographic assay for hemoglobin $A_1$ or $A_{1c}$ in a sample of human blood. The relative amounts of hemoglobin components in the composition conform approximately to the following formula:

$$y = mx + b$$
where $y$ = weight percent $A_{1c}$ with respect to $A_1$
$x$ = weight percent $A_1$ with respect to total hemoglobin
$m = -1.7$ and $b = 85$ when $x < 10$, and
$m = -1.2$ and $b = 80$ when $x > 10$.

The compositions when analyzed in a cation exchange assay produce a result which varies with temperature in substantially the same manner as that from a true sample of human blood.

20 Claims, No Drawings

COMPOSITIONS AND METHOD FOR CORRECTING TEMPERATURE DEPENDENCE OF HEMOGLOBIN ASSAYS

BACKGROUND OF THE INVENTION

1. Field of the Invention

This invention relates to assay methods which involve the separation of glycosylated from non-glycosylated hemoglobins by ion exchange column chromatography, and specifically to means for correcting the results of such assays for variations in temperature. The measurement of glycosylated hemoglobin serves as a time-averaged indicator of blood glucose levels in patients afflicted with diabetes mellitus.

The level of hemoglobin $A_1$ (Hb$A_1$), a glycosylated form of adult hemoglobin (HbA), is known to be higher in the blood of diabetic persons than in that of normal persons. Hemoglobin $A_1$, is composed of at least three subfractions, Hb$A_{1a}$, Hb$A_{1b}$, and Hb$A_{1c}$. These three subfractions account for about seven percent of the total hemoglobin in the normal adult with Hb$A_{1c}$ being the major subfraction. Each of these fractions contributes to the observed increase. Therefore, assays for Hb$A_1$ in the aggregate as well as those specific for Hb$A_{1c}$ are used to monitor carbohydrate control in diabetic patients. Ion exchange separation techniques which isolate the hemoglobin component or components of interest from the remaining components have been found to be particularly useful in this regard. A weak cation exchange column is exemplary of columns used in tests of this kind. A buffer solution which preferentially elutes the Hb$A_1$ fraction is passed through the resin, leaving nonglycosylated hemoglobins behind.

Unfortunately, the efficiency of the separation is temperature dependent. Resins for analytical use are thus formulated and prepared with a distinct operating temperature in mind, herein designated a "design" or "reference" temperature, which typically ranges from about 22° C. to about 24° C. At temperatures below the design temperature, an increasing amount of the fraction of interest (be it Hb$A_1$ or Hb$A_{1c}$) remains in the resin, whereas at higher temperatures increasing amounts of nonglycosylated hemoglobins elute off the resin in combination with the fraction of interest. To achieve comparison among samples on a common basis, therefore, it has been necessary to either impose strict temperature control to the design temperature or to use temperature conversion charts which require a highly accurate measurement of the temperature of columns and reagents during the performance of the assay.

In view of the inconvenience of such measures, it is desirable to find a method for improving the accuracy of ion exchange column chromatographic techniques for the measurement of Hb$A_1$ values which avoids both the need for highly precise temperature measurements and control.

2. Description of the Prior Art

A general discussion of glycosylated hemoglobins and their relevance to diabetes mellitus is offered by Bunn, et al., Science, 200, pp. 21–27 (1978). The use of ion exchange resins is described by Chou, et al., Clin. Chem., 24 (10), pp. 1708–1710 (1978) and in a series of U.S. Pat. Nos. to Acuff: 4,142,855, 4,142,856, 4,142,857 and 4,142,858 (all issued on Mar. 6, 1978), 4,168,147 (issued on Sept. 18, 1979) and 4,238,196 (issued on Dec. 9, 1980).

Lyophilized hemoglobin preparations stabilized with polyhydroxyl compounds are disclosed by Proksch, et al., Am. J. Clin. Pathol., 74(1), pp. 64–67 (1980), Bonderman, et al., Clin. Chem., 26(2), pp. 305–308 (1980).

SUMMARY OF THE INVENTION

Compositions are provided for the correction of a hemoglobin $A_1$ cation exchange column chromatographic assay to a reference temperature. Although artificially constituted, the compositions are unusually stable and possess the unusual ability to produce an analytical result which varies with temperature in the same manner as that of a true sample of human blood. The invention resides in the compositions, their preparation, and their methods of use.

DETAILED DESCRIPTION

The design temperatures for commercially available Hb$A_1$ assay columns vary with the source, generally ranging from about 22° C. to about 24° C. The present invention arises in part from the discovery that standardized solutions for the calibration of such columns, i.e., the correction of assay results to the design temperature, are generally unreliable, since they often fail to vary with varying temperature in the same manner as actual patient samples. By correlating the ratio of hemoglobin $A_{1c}$ to hemoglobin $A_1$ with the ratio of hemoglobin $A_1$ to total hemoglobin in a specified manner, however, one can provide a standardized calibration solution (hereinafter, "calibrator") which responds to temperature variations in a manner substantially identical to patient samples. With this discovery, one can now prepare and use calibrators to alleviate temperature variations in cation exchange assays for the hemoglobin $A_1$ content of human blood.

It has further been discovered that hemoglobin compositions of unusually high storage stability can be prepared by a procedure which comprises washing red blood cells with cold isotonic saline solution, lysing the cells and isolating the lysate from cell membranes and unlysed cells, filtering the lysate through a filter of less than about 1.0 micron pore size, adding to the lysate effective amounts of at least one antibiotic, dialyzing the lysate against dilute ethylenediaminetetraacetic acid, separating the lysate into a plurality of fractions by ion exchange chromatography, dialyzing the fractions against dilute ethylenediaminetetraacetic acid (EDTA), recombining the fractions to achieve standard compositions of the desired component ratios, adding an effective amount of a polyhydroxyl compound, and lyophilizing said compositions in a two-stage lyophilization procedure. To provide artificially constituted storage-stable compositions which respond to temperature variations in an ion exchange column chromatographic assay in a manner substantially identical to patient samples, the two hemoglobin ratios mentioned above are related by the following formula:

---
$y = mx + b$
where $y$ = weight percent $A_{1c}$ with respect to total $A_1$
$x$ = weight percent $A_1$ with respect to total hemoglobin
$m = -1.7$ and $b = 85$ when $x < 10$
$m = -1.2$ and $b = 80$ when $x > 10$

---

With the relative amounts of the hemoglobins so controlled, a plurality of calibrators can be prepared for use in hemoglobin $A_1$ assays. The calibrators will be compositions varying in the ratio of hemoglobin $A_1$ to total hemoglobin, with the range of ratios extending over the expected range of the sample to be analyzed. Since the calibration curve closely approximates a straight line, useful results can be obtained with as little as two calibrators. However, for purposes of convenience and improved accuracy, a set of at least three calibrators is preferred. An example of one such set is a three-level combination, the first level having an $A_1$ to total hemoglobin ratio of about 5–8% (weight basis) to correspond to a normal (non-diabetic) patient, the second having a ratio of about 9–12% (an intermediate range) and the third having a ratio of about 13–16% (representing a diabetic patient with poor carbohydrate control). Preferred ranges are about 6–8% (first level), about 10–12% (second level), and about 14–16% (third level).

Compositions which conform to the above formula are prepared by forming a hemolysate of a sample of human blood, separating out an $A_{1c}$-rich fraction from the hemolysate by an conventional separation technique, and combining this fraction in appropriate amounts with the hemolysate and/or other separation fractions.

The hemolysis is performed on human blood which is negative for hepatitis B surface antigen. Either whole blood or red blood cells can be used. If whole blood is used, it is preferable to isolate the red blood cells; this is conveniently achieved by centrifugation. The isolated red blood cells are then washed with a cold isotonic saline solution, preferably at a temperature within the range of about 0° C. to about 10° C., to clean the cell exteriors of serum proteins. Hemolysis is then accomplished by any conventional technique. Examples are agitation, the use of organic hydrophobic solvents, osmotic shock, sonication and the use of aqueous detergents. Osmotic shock is preferred and is readily accomplished by placing the cells in sterile, filtered, deionized water and stirring for a period of several minutes.

Once hemolysis has occurred, the clear lysate is isolated from the stroma by sedimentation of the stroma and recovery of the supernatant. Sedimentation may be promoted by acidification of the hemolysate to a pH of approximately 5.7 by the addition of dilute (2 N) hydrochloric acid, followed by centrifugation. This serves to remove the stroma, contaminating proteins and unlysed red blood cells. Further clarification of the solution may be achieved by neutralizing the solution and centrifuging a second time. Conventional filtration techniques, preferably using a micropore filter of 1 micron or less pore size, are then used for clarification.

Ion exchange resins useful for the fractionation of the hemoglobin components can include any conventional cation exchange resin with a weakly acidic character. Examples of suitable resin matrices are acrylic, methacrylic and phenolic polymers, as well as polystyrene, polyvinyl compounds, cellulose and agarose. Examples of active groups of a weakly acidic character are carboxylic, methylcarboxylic and phosphoric acid groups. A preferred resin is a copolymer of methacrylic acid and divinylbenzene. The particle size of the resin is not critical and will vary with the type of column used. It will be most convenient to use particles of a size between 100 and 400 mesh (U.S. Sieve Series), preferably between 200 and 400 mesh.

When a copolymer of methacrylic acid and divinylbenzene is used, it is preferred that about 30% to about 50%, more preferably about 35% to about 45%, of the active sites on the resin are occupied by ions of an alkali metal, the remainder being occupied by hydrogen ions. The term "alkali metal" is intended to designate the metals of Group 1-A of the periodic table. Preferred metals are those with an atomic weight equal to or less than that of potassium. Of these, sodium and potassium are particularly preferred, and sodium is the most preferred. Adjustment of the ionic ratio is conveniently achieved by the use of an acidic buffer solution, e.g., phosphoric acid, and must be completed prior to impregnation.

Although any conventional configuration can be used, the resin is preferably arranged as a fixed bed in a vertical column. Impregnation is then achieved by applying the hemolysate to the top of the column and allowing it to flow through the particle interstices into the bulk of the bed.

Fractionation of the hemoglobin components is achieved by passing a buffer solution through the impregnated column, which elutes the hemoglobin $A_{1a}$ and $A_{1b}$ components in preference to the $A_{1c}$, and the $A_{1c}$ in preference to nonglycosylated components. Exemplary buffer solutions will contain alkali metal ions at a concentration within the range of about 0.02 M to about 0.08 M. As on the resin itself, alkali metals with an atomic weight equal to or less than that of potassium are preferred, with sodium and potassium particularly preferred and sodium the most preferred.

The pH of the buffer is not critical and is subject only to the need to avoid oxidation and denaturation of the hemoglobins by excess acidity and to effect the desired separation. In general, the pH will fall within the range of about 5.0 to about 7.5, preferably about 6.5 to about 7.0. Any conventional buffer system with a pH within this range can be used. Examples include biochemical buffers, zwitterionics and phosphate buffers. Preferred buffers are potassium and sodium phosphates, both monobasic and dibasic. Sodium phosphates are particularly preferred.

The temperature considerations of the separation are similar to those of any ion exchange process. The appropriate temperature will thus depend on the relative amounts of hemolysate, buffer and resin, the particle size and alkali metal content of the resin, the particle surface area and other similar variables, and can readily be determined by routine experimentation. It will be most convenient to operate the column at a temperature within the range of about 15° C. to about 25° C., preferably at about 19° C., to maintain stability of the hemoglobins.

The volume of elution buffer and its flow rate through the resin will be selected by routine experimentation to provide the optimum separation. Conventional stabilizers such as sodium azide and/or ethylenediamine tetraacetic acid can be included in the elution buffer in convenient amounts.

High hemoglobin concentrations in the eluted fractions can be detected by the observance of red color or by a spectrophotometric measurement indicating an increase in absorbance at 415 nm. The elution buffer and conditions will be selected to cause an initial fraction to appear with a high concentration of $A_{1a}$ and $A_{1b}$, followed by a subsequent fraction rich in $A_{1c}$. The fractions are then readily analyzed for their hemoglobin contents by any conventional technique, notably biochemical techniques and spectrophotometric techniques well known in the art. After the last of the glycosylated hemoglobin has eluted, the nonglycosylated hemoglobin can be collected from the column by elution with a buffer solution of high salt content. Appropriate buffer solutions are known in the art.

With properly adjusted elutions, therefore, one can collect fractions containing: (1) high concentrations of hemoglobin $A_{1a}$ and $A_{1b}$, (2) a high concentration of hemoglobin $A_{1c}$, and (3) nonglycosylated hemoglobin with at most negligible amounts of $A_{1a}$, $A_{1b}$ and $A_{1c}$. The original lysate and any fractions obtained as ion exchange column eluates are dialyzed against a dilute EDTA solution to reduce the levels of salts and other contaminants retained during the processing steps. The concentration of EDTA is not critical and generally falls within the range of about 0.05 mm to about 0.5 mm. In normal practice, the dialysate is changed several times before dialysis is complete.

The dialyzed fractions can either be combined with each other or with unseparated but dialyzed portions of the original hemolysate supernatant to provide compositions specified ratios of $A_1$ to total hemoglobin, and with amounts of $A_{1c}$:$A_1$ ratios according to the formula specified above.

Various steps can be taken to promote storage stability of the compositions, prolonging their useful life to facilitate shipping and sales. One such step, mentioned above, is the removal of serum proteins from the red blood cells prior to hemolysis. Another step is the removal of salts and other low molecular weight solutes from the hemolysate prior to the chromatographic separation. This is conveniently achieved by dialysis through a semi-permeable membrane with a molecular weight cut-off of approximately 10,000 or higher. A further step is the inclusion of antibiotics in effective amounts. Aminoglycosides are generally preferred, examples of which are gentamicin and tobramycin.

It is preferred that the compositions be lyophilized to promote ease of handling and storage. To promote the stability of the compositions during the low temperature exposure required for lyophilization, it is preferred to include a polyhydroxyl organic compound in each composition at a concentration ranging of from about 1.0 percent to about 20.0 percent by weight, preferably about 2.0 percent to about 10.0 percent by weight, with respect to the liquid solutions prior to lyophilization. Suitable polyhydroxyl organic compounds are those with a molecular weight from about 150 to about 400 daltons and containing a minimum of three hydroxyl groups. Examples include lactose, sucrose, sorbitol, mannitol, and polymers and copolymers of these. An example of the latter is Ficoll®, a copolymer of sucrose and epichlorohydrin (product of Pharmacia Fine Chemicals, Inc., New Market, N.J.). Preferred compounds are monosaccharides and disaccharides. Sucrose is particularly preferred.

Lyophilization is then accomplished by conventional techniques in a two-stage procedure. In the first stage, the temperature is gradually increased from about $-40°$ C. to about $-5°$ C. over a period of at least about 7 hours. In the second stage, the temperature is gradually increased from about $-5°$ C. to about $+5°$ C. over a period of at least about an hour and maintained at about $+5°$ C. for at least about 40 hours, until substantially all moisture has been removed.

The resulting calibrators are useful for the temperature correction of ion exchange column chromatographic assays in general for hemoglobin $A_1$ determination. A preferred assay on which the calibrators are applied is one involving a weak cation exchange resin. An example of such a resin is Bio-Rex ®70 Cation Exchanger, a copolymer of methacrylic acid and divinylbenzene with methylcarboxylic acid functional groups, a product of Bio-Rad Laboratories, Richmond, Calif. Exemplary assay materials to be used in conjunction with such an exchanger are those supplied with the "Hemoglobin $A_1$ by Column Test" kit, which has a reference temperature of 22° C., and is also a product of Bio-Rad Laboratories. A typical assay procedure comprises (a) lysing the red blood cells in a blood sample to form a hemolysate, (b) impregnating the ion exchanger with the hemolysate, (c) preferentially eluting hemoglobin $A_1$ from the exchanger by passing therethrough a buffer solution with alkali metal ions dissolved therein at a concentration of from about 0.06 M to about 0.11 M, and (d) analyzing the eluate for its hemoglobin $A_1$ content.

The calibrators are used to develop a calibration curve by performing elutions on them under the same conditions as those under which the samples themselves will be run, i.e., in the same environment and either concurrently or close in time. Lyophilized calibrators can be dissolved in appropriate amounts of sterile water prior to use. The hemoglobin $A_1$ fraction of each calibrator as determined by the assay procedure is then correlated with the predetermined values of the calibrators (i.e., the values at the reference temperature). The result is a substantially straight line. Assay results from actual patient samples are then determined and corrected to their reference temperature equivalents, using the calibration curve.

In addition to their temperature-correcting capability, the calibrators of the present invention are further useful in correcting for other systematic errors in the assay procedure, as for example when a precise volume measurement is required and a piece of apparatus which is defective due to an inaccurate volume indicator is used.

The following examples are offered to further illustrate the invention and are intended neither to limit nor define the invention in any manner.

EXAMPLE 1

PREPARATION OF CALIBRATORS

1. Hemolysate Preparation

Whole human blood which was negative for Hepatitis B Surface Antigen was centrifuged at 3000 RPM (1700×g) for 30 min. in 1-liter tubes at 2°–8° C. to sediment the red blood cells. The plasma was then aspirated off and the cells washed four times with isotonic saline solution (0.15 M NaCl) at 2°–8° C. Supernants were removed by aspiration.

The washed red blood cells were pooled and lysed by addition of an equal weight of sterile-filtered deionized water for 5 min. with stirring. Dilute HCl (2.0 N) was then added to adjust the pH to 5.7±0.1, and the hemolysate was mixed for an additional 15 min., then centrifuged as above for 60 min. Stroma, contaminating proteins and unlysed cells were pelleted and discarded. The pH was then raised to 7.0±0.1 with dilute NaOH (2.0 N) over a ten-minute period and further centrifuged for 30 min.

The hemolysate was then filtered in a laminar flow hood through a prefilter and a 0.45 micron filter, collected in a polycarbonate container on ice and wrapped in aluminum foil to preclude light. Potassium cyanide was added to a level of 0.01% (weight/volume), followed by stirring on ice for ten minutes. Gentamicin and tobramycin were added to 0.0004% (weight/volume) each. Finally, ethylene diamine tetraacetic acid (EDTA) was added to a concentration of 0.1 mM.

The hemolysate was then dialyzed with stirring against a 1:100 volume of 0.1 mM EDTA, using standard cellulose tubing with molecular weight cut-off of 12,000–14,000, for 24 hours.

2. Column Enrichment

Two 10×50 cm water-jacketed chromatographic columns were packed with Bio-Rex ®70 ion exchange resin (a copolymer of methacrylic acid and divinylbenzene with methyl carboxylic acid groups, obtained from Bio-Rad Laboratories, Richmond, Calif.) in which 35–45% of the functional sites were occupied by sodium ions, the remainder being occupied by hydrogen ions. The packed columns were washed with sterile-filtered deionized water and maintained at 19° C.

Each column was washed with 1.5 L of a low salt buffer solution consisting of 20 mM sodium phosphate and 0.1 mM EDTA at pH 6.85. A portion of the dialyzed hemolysate from the preceding section was applied onto each column (2800 ml per column). The columns were then washed with the low salt buffer until the eluate was nearly colorless or showed low absorbance at 415 nm.

A second eluate was then collected using a high salt buffer (20 mM sodium phosphate, 0.1 mM EDTA, 0.4 M NaCl, pH 6.85) until a color or absorbance change was observed. Antibiotics were added and the eluate was dialyzed against 1:100 volumes of 0.1 mM EDTA for several days. Further antibiotics were then added. Concentrations of $HbA_1$ and $HbA_{1c}$ were then determined using the Bio-Rad Hemoglobin $A_1$ by Column Test.

Portions of the eluates were then combined with portions of the hemolysate from Section 1 above or with each other to provide three compositions as follows, each of which conform to the formula recited above:

TABLE 1

| CALIBRATION STANDARDS | | |
|---|---|---|
| Level | x | y |
| 1 | 6.7 | 74.0 |
| 2 | 10.9 | 66.9 |
| 3 | 14.8 | 62.2 | x = weight % $A_1$ with respect to total hemoglobin
y = weight % $A_{1c}$ with respect to $A_1$ The standards were then supplemented with the following: 0.0004% (weight/volume) antibiotics, 0.1 mM EDTA, 5% (weight/volume) sucrose. The resulting solutions were sterile-filtered through a 0.2-micron filtration system and placed in vials.

3. Lyophilization

The calibrators standards were frozen at −20° C., then lowered to −40° C. to −50° C. and permitted to equilibrate. Lyophilization was then performed on the calibrators as follows: 4 hours at −40° C., 3 hours at −40° C. to −5° C., one hour at −5° C. to +5° C., and 48 to 60 hours at +5° C.

EXAMPLE 2

TEST RESULTS

Ten patient samples were analyzed for $HbA_1$ as percent of total hemoglobin. The analyses were performed at 19° C., 22° C. and 30° C. The 19° C. and 30° C. values were then corrected to 22° C. using three separate calibration curves, each derived from a set of three calibrators prepared as in Example 1. The corrected values were then plotted against the actual 22° C. values for each temperature and set of calibrators, to determine the correlation of coefficient, the slope, and the intercept.

The calibrators were constituted as follows, each calibrator conforming to the formula recited above, within experimental error:

TABLE 2

| EXPERIMENTAL CALIBRATOR SETS | | | |
|---|---|---|---|
| SET | LEVEL | x (weight %) | y (weight %) |
| A | 1 | 6.5 | 73.7 |
|   | 2 | 10.1 | 67.8 |
|   | 3 | 14.6 | 63.4 |
| B | 1 | 6.4 | 74.5 |
|   | 2 | 9.6 | 68.8 |
|   | 3 | 14.0 | 61.7 |
| C | 1 | 6.2 | 72.3 |
|   | 2 | 10.1 | 68.0 |
|   | 3 | 13.9 | 62.2 |

The results are shown in Tables 3 and 4, where the ideal plot of corrected 22° C. values to actual 22° C. values is a straight line with slope of 1.0 and intercept of zero.

TABLE 3

TEST RESULTS AT 19° C.
RATIO $HbA_1$ TO TOTAL HEMOGLOBIN
(WEIGHT PERCENTS)

| PA-TIENT NO. | ACTUAL 22° C. VALUES | OBSERVED 19° C. VALUES | 19° VALUES CORRECTED TO 22° C. CALIBRATOR SETS: | | |
|---|---|---|---|---|---|
| | | | A | B | C |
| AG | 6.98 | 6.25 | 7.28 | 6.97 | 6.97 |
| BG | 9.23 | 8.10 | 9.2 | 9.02 | 9.06 |
| CG | 8.65 | 7.54 | 8.63 | 8.42 | 8.44 |
| DG | 7.83 | 6.84 | 7.9 | 7.64 | 7.64 |
| EG | 7.33 | 6.68 | 7.7 | 7.43 | 7.43 |
| 61 | 18.12 | 16.86 | 18.8 | 18.33 | 18.5 |
| 62 | 17.73 | 16.53 | 18.43 | 18.0 | 18.12 |
| 63 | 16.34 | 14.90 | 16.61 | 16.3 | 16.45 |
| 64 | 18.36 | 16.94 | 18.9 | 18.4 | 18.6 |
| 65 | 11.03 | 10.26 | 11.5 | 11.41 | 11.5 |

| For Plot of Values Corrected to 22° vs. Actual 22° C. Values: | | | |
|---|---|---|---|
| Calibrator Set | A | B | C |
| Correlation Coefficient | 0.999 | 0.999 | 0.999 |
| Slope | 1.039 | 1.020 | 1.035 |
| Intercept | −0.14 | −0.21 | −0.31 |

TABLE 4

TEST RESULTS AT 30° C.
RATIO $HbA_1$ TO TOTAL HEMOGLOBIN
(WEIGHT PERCENTS)

| PA-TIENT NO. | ACTUAL 22° C. VALUES | OBSERVED 30° C. VALUES | 30° C. VALUES CORRECTED TO 22° C. CALIBRATOR SETS: | | |
|---|---|---|---|---|---|
| | | | A | B | C |
| AG | 6.98 | 9.18 | 7.2 | 7.12 | 6.98 |
| BG | 9.23 | 12.04 | 9.42 | 9.61 | 9.30 |
| CG | 8.65 | 11.28 | 8.81 | 8.92 | 8.67 |
| DG | 7.83 | 10.21 | 8.0 | 8.05 | 7.81 |
| EG | 7.33 | 9.62 | 7.55 | 7.55 | 7.35 |
| 61 | 18.12 | 21.44 | 17.06 | 17.30 | 16.9 |
| 62 | 17.73 | 20.53 | 17.0 | 17.22 | 16.8 |
| 63 | 16.34 | 20.65 | 17.0 | 17.25 | 16.8 |
| 64 | 18.36 | 22.53 | 18.23 | 18.45 | 18.1 |

TABLE 4-continued
TEST RESULTS AT 30° C.
RATIO HbA$_1$ TO TOTAL HEMOGLOBIN
(WEIGHT PERCENTS)

| 65 | 11.03 | 13.96 | 10.9 | 11.22 | 10.83 |
|---|---|---|---|---|---|

For Plot of Values Corrected to
22° vs. Actual 22° C. Values:

| Calibrator Set | A | B | C |
|---|---|---|---|
| Correlation Coefficient | 0.996 | 0.996 | 0.996 |
| Slope | 0.942 | 0.961 | 0.943 |
| Intercept | 0.66 | 0.59 | 0.49 |

EXAMPLE 3

COMPARATIVE TESTS

To demonstrate the unusual nature of calibrators which conform to the formula recited above, three sets of calibrators were constituted (D, E, and F), only one of which conformed substantially to the formula (Set F). The compositions of each set are listed in Table 3. Comparative test results at 19° C. and 30° C. are listed in Tables 4 and 5. Comparison of the slopes and intercepts show that set F is superior in each case.

TABLE 5
EXPERIMENTAL CALIBRATOR SETS

| SET | LEVEL | x (weight %) | y (weight %) |
|---|---|---|---|
| D | 1 | 7.2 | 65.4 |
|   | 2 | 10.3 | 73.2 |
|   | 3 | 13.0 | 64.1 |
| E | 1 | 6.7 | 75.0 |
|   | 2 | 10.2 | 73.2 |
|   | 3 | 13.7 | 66.8 |
| F | 1 | 5.8 | 74.8 |
|   | 2 | 10.8 | 67.1 |
|   | 3 | 14.6 | 62.2 | x = ratio of HbA$_1$ to total hemoglobin
y = ratio of HbA$_{1c}$ to HbA$_1$

TABLE 6
TEST RESULTS AT 19° C.
RATIO HbA$_1$ TO TOTAL HEMOGLOBIN
(AS WEIGHT PERCENTS)

| PATIENT NO. | ACTUAL 22° C. VALUES | OBSERVED 19° C. VALUES | 19° C. VALUES CORRECTED TO 22° C. CALIBRATOR SETS: | | |
|---|---|---|---|---|---|
| | | | D | E | F |
| 1001 | 9.19 | 6.70 | 9.26 | 9.65 | 9.13 |
| 1002 | 6.90 | 5.24 | 7.71 | 7.86 | 7.36 |
| 1003 | 5.93 | 3.65 | 6.02 | 5.90 | 5.44 |
| 1004 | 7.14 | 5.42 | 7.40 | 8.08 | 7.58 |
| 1005 | 6.65 | 4.52 | 6.94 | 6.27 | 6.49 |
| 1006 | 15.82 | 11.73 | 14.59 | 15.84 | 15.21 |
| 1007 | 19.05 | 14.66 | 17.64 | 19.45 | 18.75 |
| 1008 | 14.66 | 10.85 | 13.66 | 14.76 | 14.14 |
| 1009 | 15.49 | 11.90 | 14.78 | 16.06 | 15.41 |
| 1010 | 8.12 | 6.13 | 8.65 | 8.95 | 8.44 |

For Plot of Values Corrected to 22° C.
vs. Actual 22° C. Values:

| Calibrator Set | D | E | F |
|---|---|---|---|
| Correlation Coefficient | 0.997 | 0.997 | 0.997 |
| Slope | 0.84 | 0.97 | 0.96 |
| Intercept | 1.58 | 0.75 | 0.38 |

TABLE 7
TEST RESULTS AT 30° C.
RATIO HbA$_1$ TO TOTAL HEMOGLOBIN
(AS WEIGHT PERCENTS)

| PATIENT NO. | ACTUAL 22° C. VALUES | OBSERVED 30° C. VALUES | 30° C. VALUES CORRECTED TO 22° C. CALIBRATOR SETS: | | |
|---|---|---|---|---|---|
| | | | D | E | F |
| 1001 | 9.19 | 11.96 | 7.9 | 9.0 | 8.8 |
| 1002 | 6.90 | 9.74 | 6.25 | 7.16 | 6.7 |
| 1003 | 5.93 | 8.19 | 5.1 | 5.88 | 5.3 |
| 1004 | 7.14 | 9.99 | 6.4 | 7.3 | 7.0 |
| 1005 | 6.65 | 9.19 | 5.85 | 6.71 | 6.2 |
| 1006 | 15.82 | 19.34 | 14.0 | 15.1 | 16.8 |
| 1007 | 19.05 | 22.23 | 13.8 | 17.9 | 18.6 |
| 1008 | 14.66 | 17.66 | 12.3 | 13.7 | 14.6 |
| 1009 | 15.49 | 18.48 | 12.95 | 14.5 | 15.1 |
| 1010 | 8.12 | 12.26 | 8.15 | 9.24 | 9.1 |

For Plot of Values Corrected to 22° C.
vs. Actual 22° C. Values:

| Calibrator Set | D | E | F |
|---|---|---|---|
| Correlation Coefficient | 0.99 | 0.995 | 0.993 |
| Slope | 0.76 | 0.88 | 1.01 |
| Intercept | 1.07 | 1.11 | −0.22 |

The foregoing description and examples are offered solely for purposes of illustration, and are not intended to limit the scope of the invention. Numerous modifications and variations from the above which still fall within the spirit and scope of the invention as claimed hereinbelow will be readily apparent to those skilled in the art.

What is claimed is:

1. A set of storage-stable hemoglobin compositions for use in the temperature correction of a hemoglobin A$_1$ or A$_{1c}$ assay of a sample performed on a cation exchange chromatographic column, said set comprising a plurality of compositions of hemoglobin A$_o$ and hemoglobin A$_1$ containing hemoglobin A$_{1c}$, said compositions containing known ratios of hemoglobin A$_1$ to total hemoglobin at graduated levels extending over the expected range of said sample, with the hemoglobin A$_{1c}$ content of the hemoglobin A$_1$ in each composition adjusted approximately according to the following formula:

$$y = mx + b$$
where y = weight percent A$_{1c}$ with respect to A$_1$,
x = weight percent A$_1$ with respect to total hemoglobin
m = −1.7 and b = 85 when x < 10, and
m = −1.2 and b = 80 when x > 10, and said compositions further containing effective amounts of at least one antibiotic agent.

2. A set of storage-stable hemoglobin compositions for use in the temperature correction of a hemoglobin A$_1$ or A$_{1c}$ assay of a sample performed on a cation exchange chromatographic column consisting essentially of a copolymer of methacrylic acid and divinylbenzene containing active sites of which about 30% to about 50% are occupied by ions of an alkali metal, to a reference temperature of from about 22° C. to about 24° C., said set comprising a plurality of compositions of hemoglobin A$_o$ and hemoglobin A$_1$ containing hemoglobin A$_{1c}$, said compositions containing known ratios of hemoglobin A$_1$ to total hemoglobin at graduated levels extending over the expected range of said sample, with the hemoglobin A$_{1c}$ content of the hemoglobin A$_1$ in each composition adjusted approximately according to the following formula:

$$y = mx + b$$
where $y$ = weight percent $A_{1c}$ with respect to $A_1$,
$x$ = weight percent $A_1$ with respect to total hemoglobin
$m = -1.7$ and $b = 85$ when $x < 10$, and
$m = -1.2$ and $b = 80$ when $x > 10$, and said compositions further containing effective amounts of at least one antibiotic agent.

3. A set of storage-stable hemoglobin compositions for use in the temperature correction of a hemoglobin $A_1$ or $A_{1c}$ assay of a sample performed on a cation exchange chromatographic column consisting essentially of a copolymer of methacrylic acid and divinylbenzene containing active sites of which about 35% to about 45% are occupied by sodium ions, to a reference temperature of about 22° C., said set comprising a plurality of compositions of hemoglobin $A_o$ and hemoglobin $A_1$ containing hemoglobin $A_{1c}$, said compositions containing known ratios of hemoglobin $A_1$ to total hemoglobin at graduated levels extending over the expected range of said sample, with the hemoglobin $A_{1c}$ content of the hemoglobin $A_1$ in each composition adjusted approximately according to the following formula:

$$y = mx + b$$
where $y$ = weight percent $A_{1c}$ with respect to $A_1$,
$x$ = weight percent $A_1$ with respect to total hemoglobin
$m = -1.7$ and $b = 85$ when $x < 10$, and
$m = -1.2$ and $b = 80$ when $x > 10$, and said compositions further containing effective amounts of at least one antibiotic agent.

4. A set of compositions according to claims 1, 2, or 3 in which said set comprises at least three compositions, the first having a value of x ranging from about 5% to about 8%, the second having a value of x ranging from about 9% to about 12%, and the third having a value of x ranging from about 13% to about 16%.

5. A set of compositions according to claims 1, 2, or 3 in which said set comprises three compositions, the first having a value of x ranging from about 6% to about 8%, the second having a value of x ranging from about 10% to about 12%, and the third having a value of x ranging from about 14% to about 16%.

6. A set of compositions according to claims 1, 2, or 3 wherein said compositions are lyophilized and each further contains an amount of a polyhydroxyl organic compound effective to promote stability of the compositions at low temperatures.

7. A set of compositions according to claims 1, 2, or 3 wherein said compositions are lyophilized and each further contains from about 1.0% to about 20.0% by weight of a polyhydroxyl organic compound with molecular weight from about 150 to about 400 daltons and containing at least three hydroxyl groups per molecule.

8. A set of compositions according to claims 1, 2, or 3 wherein said compositions are lyophilized and each further contains from about 2.0% to about 10.0% by weight of a polyhydroxyl organic compound selected from the group consisting of monosaccharides and disaccharides.

9. A set of compositions according to claims 1, 2, or 3 wherein said compositions are lyophilized and each further contains from about 2.0% to about 10.0% by weight of a polyhydroxyl compound selected from the group consisting of lactose, sucrose, sorbitol, mannitol, and a copolymer of sucrose and epichlorohydrin.

10. A set of compositions according to claims 1, 2, or 3 wherein said compositions are lyophilized and each further contains from about 2.0% to about 10.0% by weight of sucrose.

11. In a method for determining the level of hemoglobin $A_1$ in a sample of human blood, which comprises:
(a) lysing the red blood cells in said sample to form a hemolysate,
(b) impregnating a weak cation exchange resin with said hemolysate,
(c) passing through said resin a buffer solution with ions of an alkali metal dissolved therein at a concentration of from about 0.06 M to about 0.11 M to preferentially elute said hemoglobin $A_1$ over other hemoglobins present in said hemolysate, and
(d) analyzing the eluate from step (c) for its hemoglobin content, the improvement comprising performing the following steps under substantially identical ambient conditions as those under which steps (b) through (d) above were performed:
(e) impregnating each of a plurality of further cation exchange resins substantially identical to that of step (b) with an aqueous calibrator solution selected from a series of such solutions such that the calibrators used contain known graduated ratios of hemoglobin $A_1$ to total hemoglobin extending over the expected range of said sample, and the composition of said calibrators conforming approximately to the following formula:

$$y = mx + b$$
where $y$ = weight percent $A_{1c}$ with respect to $A_1$
$x$ = weight percent $A_1$ with respect to total hemoglobin
$m = 1.7$ and $b = 85$ when $x < 10$, and
$m = 1.2$ and $b = 80$ when $x > 10$, (f) passing through each of the resins of step (e) a buffer solution identical to that of step (c),
(g) analyzing each of the eluates from step (f) for its hemoglobin content, and
(h) comparing the analysis of step (d) with those of step (g).

12. A method according to claim 11 in which the number of calibrator solutions used in step (c) is at least three, the first having a value of x ranging from about 5% to about 8%, the second having a value of x ranging from about 9% to about 12%, and the third having a value of x ranging from about 13% to about 16%.

13. A method according to claim 11 in which the number of calibrator solutions used in step (c) is at least three, the first having a value of x ranging from about 6% to about 8%, the second having a value of x ranging from about 10% to about 12%, and the third having a value of x ranging from about 14% to about 16%.

14. A method according to claims 11, 12, or 13 in which the calibrator solutions of step (e) are prepared from lyophilized compositions which further contain an amount of a polyhydroxyl organic compound effective to promote stability of the compositions at low temperatures.

15. A method according to claims 11, 12, or 13 in which the calibrator solutions of step (e) are prepared from lyophilized compositions which further contain from about 1.0% to about 20.0% by weight of a polyhydroxyl organic compound with molecular weight from about 150 to about 400 daltons and containing at least three hydroxyl groups per molecule.

16. A method according to claims 11, 12, or 13 in which the calibrator solutions of step (e) are prepared from lyophilized compositions which further contain from about 2.0% to about 10.0% by weight of a polyhydroxyl organic compound selected from the groups consisting of monosaccharides and disaccharides.

17. A method according to claims 11, 12, or 13 in which the calibrator solutions of step (e) are prepared from lyophilized compositions which further contain from about 2.0% to about 10.0% by weight of a polyhydroxyl compound selected from the group consisting of lactose, sucrose, sorbitol, mannitol, and a copolymer of sucrose and epichlorohydrin.

18. A method according to claims 11, 12, or 13 in which the calibrator solutions of step (e) are prepared from lyophilized compositions which further contain from about 2.0% to about 10.0% by weight of sucrose.

19. A method for the preparation of storage-stable hemoglobin compositions which comprises:
  (a) isolating red blood cells from a sample of human blood,
  (b) washing said cells with cold isotonic saline solution,
  (c) lysing said cells to form a lysate,
  (d) isolating a clear supernatant solution from said lysate,
  (e) filtering said solution through a filter less than about 1.0 micron pore size,
  (f) adding an effective amount of at least one antibiotic to said solution,
  (g) dialyzing said solution against dilute ethylenediaminetetraacetic acid,
  (h) separating said solution into a plurality of fractions by ion exchange chromatography,
  (i) dialyzing said fractions against dilute ethylenediaminetetraacetic acid,
  (j) recombining said fractions to achieve standard compositions of predetermined hemoglobin component ratios, adding an effective amount of a polyhydroxyl compound, and
  (k) lyophilizing said compositions at a temperature gradually increasing from about $-40°$ C. to about $-5°$ C. over a period of at least about seven hours, followed by a temperature gradually increasing from about $-5°$ C. to about $+5°$ C. over a period of at least about one hour, and then maintained at about $+5°$ C. for at least about forty hours.

20. A method according to claim 19 in which step (b) is performed at a temperature of from about $0°$ C. to about $10°$ C., step (c) is accomplished by stirring said cells in sterile, filtered, deionized water, the antibiotic of step (f) consists of at least one aminoglycoside, the dilute ethylenediaminetetraacetic acid of steps (g) and (i) are aqueous solutions of a concentration of from about 0.05 mM to about 0.5 mM, step (h) is accomplished by the use of an ion exchange column consisting essentially of a copolymer of methacrylic acid and divinylbenzene containing active sites of which about 30% to about 50% are occupied by sodium ions, and the polyhydroxyl compound of step (j) is sucrose at a concentration of from about 2.0 percent to about 10.0 percent by weight.

* * * * *